US00PP32597P2

(12) United States Plant Patent
Yamada

(10) Patent No.: US PP32,597 P2
(45) Date of Patent: Dec. 8, 2020

(54) ***PETUNIA* PLANT NAMED 'SUNPETU 761'**

(50) Latin Name: ***Petunia* x *hybrida***
Varietal Denomination: Sunpetu 761

(71) Applicant: Masahiro Yamada, Shiga (JP)

(72) Inventor: Masahiro Yamada, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 16/873,397

(22) Filed: Apr. 4, 2020

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.1, 356.13
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Sunpetu 761', characterized by its mounding and trailing plant habit; vigorous growth habit; freely branching habit; freely flowering habit; long flowering period; flowers that are white in color with a red purple-colored cordate-shaped pattern; and good garden performance.

1 Drawing Sheet

Figure 1:
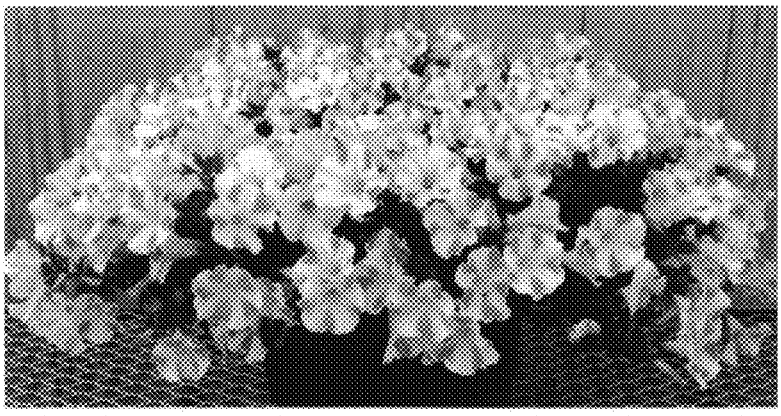

Botanical designation: *Petunia* x *hybrida*.
Cultivar denomination: 'SUNPETU 761'.

BACKGROUND OF THE INVENTION

The present invention relates to a new and distinct cultivar of *Petunia* plant, botanically known as *Petunia* x *hybrida* and hereinafter referred to by the name 'Sunpetu 761'.

The new *Petunia* plant is a product of a planned breeding program conducted by the Inventor in Higashiomi, Shiga, Japan. The objective of the breeding program is to create new vigorous, trailing and freely-flowering *Petunia* plants with attractive flower colors and patterns.

The new *Petunia* plant originated from a cross-pollination made by the Inventor in July, 2013 in Higashiomi, Shiga, Japan of a proprietary selection of *Petunia* x *hybrida* identified as code number MP24-125-2, not patented, as the female, or seed, parent with a proprietary selection of *Petunia* x *hybrida* identified as code number MP25-125-2, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in July, 2014.

Asexual reproduction of the new *Petunia* plant by terminal vegetative cuttings in a controlled greenhouse environment in Higashiomi, Shiga, Japan since January, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunpetu 761'. These characteristics in combination distinguish 'Sunpetu 761' as a new and distinct *Petunia* plant:

1. Mounding and trailing plant habit.
2. Vigorous growth habit.
3. Freely branching habit.
4. Freely flowering habit.
5. Long flowering period.
6. Flowers that are white in color with a red purple-colored cordate-shaped pattern.
7. Good garden performance.

Plants of the new *Petunia* can be compared to plants of the female parent selection. Plants of the new *Petunia* differ primarily from plants of the female parent selection in flower color as plants of the new *Petunia* have white-colored flowers with a red purple-colored cordate pattern whereas plants of the female parent selection have white-colored flowers with a purple-colored picotee pattern.

Plants of the new *Petunia* can be compared to plants of the male parent selection. Plants of the new *Petunia* differ primarily from plants of the male parent selection in flower color as plants of the new *Petunia* have white-colored flowers with a red purple-colored cordate pattern whereas plants of the male parent selection have white-colored flowers with a light pink-colored cordate pattern.

Plants of the new *Petunia* can also be compared to plants of the *Petunia* x *hybrida* 'Sunmomoheart', disclosed in U.S. Plant Pat. No. 28,290. In side-by-side comparisons, plants of the new *Petunia* and 'Sunmomoheart' differ primarily in the following characteristics:

1. Plants of the new *Petunia* are more trailing than and not as mounding as plants of 'Sunmomoheart'.
2. Plants of the new *Petunia* are broader than plants of 'Sunmomoheart'.
3. Leaves of plants of the new *Petunia* are darker green than leaves of plants of 'Sunmomoheart'.
4. Plants of the new *Petunia* are more freely flowering than plants of 'Sunmomoheart'.

5. Flower petals of plants of the new *Petunia* are broader than flower petals of plants of 'Sunmomoheart'.
6. Flowers of plants of the new *Petunia* have a larger cordate pattern than flowers of plants of 'Sunmomoheart'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet (FIG. 1 of 2) is a side perspective view of a typical flowering plant of 'Sunpetu 761' grown in a container.

Figure 2:
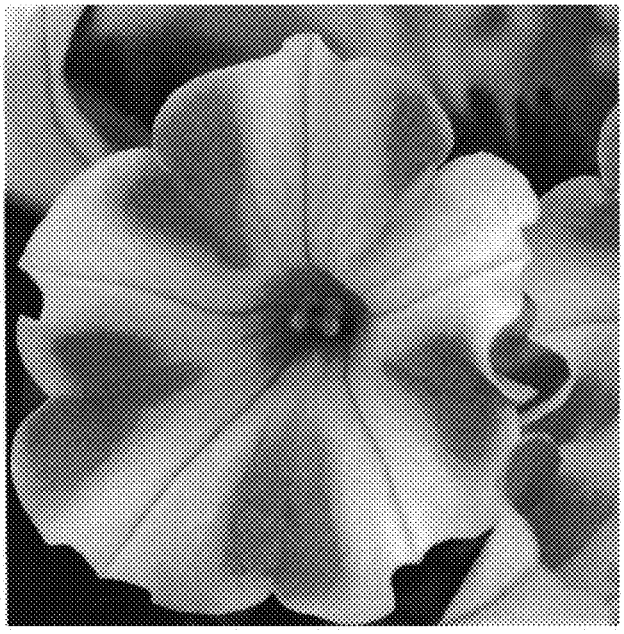

The photograph at the bottom of the sheet (FIG. 2 of 2) is a close-up view of a typical flowering plant of 'Sunpetu 761'.

DETAILED BOTANICAL DESCRIPTION

The aforementioned photographs and following observations, measurements and values describe plants grown during the spring in 24-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six months old when the photographs and description were taken. In the following description, color references are made to The Royal Horticultural Society Colour Chart, 2015 Edition, except where general terms of ordinary dictionary significance are used.

Botanical classification: *Petunia* x *hybrida* 'Sunpetu 761'.

Parentage:

*Female, or seed, parent*.—Proprietary selection of *Petunia* x *hybrida* identified as code number MP24-125-2not patented.

*Male, or pollen, parent*.—Proprietary selection of *Petunia* x *hybrida* identified as code number MP25-125-2, not patented.

Propagation:

*Type*.—By terminal vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Mounding and trailing plant habit; freely branching habit with numerous lateral branches developing per plant; pinching enhances lateral branch development; vigorous growth habit.

*Plant height*.—About 22 cm.

*Plant diameter*.—About 73 cm.

Lateral branch description:

*Length*.—About 19.8 cm.

*Diameter*.—About 2.3 mm.

*Internode length*.—About 2.4 cm.

*Strength*.—Strong, flexible.

*Aspect*.—Mostly outwardly.

*Texture*.—Densely pubescent, rough and viscid.

*Color*.—Close to 144A.

Leaf description:

*Quantity and arrangement*.—About twelve leaves per lateral branch; alternate, simple.

*Length*.—About 3.4 cm.

*Width*.—About 2.3 cm.

*Shape*.—Elliptical.

*Apex*.—Broadly acute.

*Base*.—Attenuate.

*Margin*.—Entire.

*Texture, upper and lower surfaces*.—Pubescent, rough and viscid.

*Venation pattern*.—Pinnate; reticulate.

*Color*.—Developing leaves, upper surface: Close to 137D. Developing leaves, lower surface: Close to 138A. Fully expanded leaves, upper surface: Close to NN137A; venation, close to 143C. Fully expanded leaves, lower surface: Close to 137C; venation, close to 144A.

*Petioles*.—Length: About 3 mm. Diameter: About 1.9 mm. Texture, upper and lower surfaces: Pubescent, rough. Color, upper and lower surfaces: Close to 144A.

Flower description:

*Flower arrangement and habit*.—Single-type salver-form flowers arising from upper leaf axils; freely flowering habit with usually about six flowers developing per lateral branch and about 204 flowers developing per plant during the flowering season; flowers face mostly upright to outwardly.

*Fragrance*.—None detected.

*Natural flowering season*.—Early flowering habit; plants of the new *Petunia* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Length: About 3.6 cm. Diameter: About 7.2 mm. Shape: Cylindrical. Color: Close to 149D; towards the apex, close to 68C and venation, close to 145C.

*Flower diameter*.—About 5 cm.

*Flower height*.—About 1.3 cm.

*Flower tube length*.—About 2.5 cm.

*Flower tube diameter, proximally*.—About 3 mm.

*Flower tube diameter, distally*.—About 1 cm.

*Corolla*.—Quantity and arrangement: Five in a single whorl, fused at the base and opening into a flared trumpet. Petal length from throat: About 1.75 cm. Petal width: About 2.4 cm. Petal shape: Roughly spatulate. Petal apex: Cuspidate. Petal margin: Entire; moderately undulate. Petal texture, upper and lower surfaces: Smooth, glabrous; velvety. Throat texture: Smooth, glabrous. Tube texture: Pubescent. Color: Petal, when opening, upper surface: Main color, close to NN155C; cordate pattern, close to 63C. Petal, when opening, lower surface: Main color, close to NN155C; cordate pattern, close to 62C. Petal, fully opened, upper surface: Main color, close to NN155C; cordate pattern, close to 63B; venation, close to 140C; colors do not change with development. Petal, fully opened, lower surface: Main color, close to NN155D; cordate pattern, close to 62C; venation is faintly visible, close to 145C to 145D; colors do not change with development. Throat: Distally, close to 150D; center, close to 145D; proximally, close to 145C; venation is faintly visible, close to 145D. Tube: Distally, close to 150D; center, close to 149D; proximally, close to 145C; venation is faintly visible, close to 145C.

*Calyx*.—Arrangement: Star-shaped calyx tube with five sepals arranged in a single whorl and fused at the base. Sepal length: About 9.5 mm. Sepal width: About 2.5 mm. Sepal shape: Lanceolate. Sepal apex: Obtuse. Sepal margin: Entire. Sepal texture, upper and lower surfaces: Pubescent. Color, upper surface: Close to 137B. Color, lower surface: Close to 137D.

*Peduncles*.—Length: About 1.3 cm. Diameter: About 1 mm. Strength: Strong, flexible. Aspect: Upright to outwardly. Texture: Pubescent, rough and viscid. Color: Close to 144B.

*Reproductive organs*.—Stamens: Quantity per flower: Five. Filament length: About 1.7 cm. Filament color: Close to 150D. Anther shape: Ellipsoidal. Anther size: About 2 mm by 2.1 mm. Anther color: Close to 158C. Pollen amount: Abundant. Pollen color: Close to NN155A. Pistils: Quantity per flower: One. Pistil length: About 2 cm. Style color: Close to 144B. Stigma shape: Transversely ellipsoidal. Stigma color: Close to 145A. Ovary color: Close to 145B. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: To date, plants of the new *Petunia* have not been observed to be resistant to pathogens and pests common to *Petunia* plants.

It is claimed:

1. A new and distinct *Petunia* plant named 'Sunpetu 761' as illustrated and described.

* * * * *